(12) United States Patent
Pistilli et al.

(10) Patent No.: US 11,006,071 B2
(45) Date of Patent: May 11, 2021

(54) INTEGRATED TELEMEDICINE DEVICE

(71) Applicant: Iron Bow Technologies, LLC, Chantilly, VA (US)

(72) Inventors: Peter Pistilli, Leesburg, VA (US); Anthony Mines, Sterling, VA (US)

( * ) Notice: Subject to any disclaimer, the term of this patent is extended or adjusted under 35 U.S.C. 154(b) by 476 days.

(21) Appl. No.: 15/439,168

(22) Filed: Feb. 22, 2017

(65) Prior Publication Data
US 2017/0244932 A1   Aug. 24, 2017

Related U.S. Application Data

(60) Provisional application No. 62/299,413, filed on Feb. 24, 2016.

(51) Int. Cl.
*H04N 7/14* (2006.01)
*G16H 40/67* (2018.01)

(52) U.S. Cl.
CPC ............. *H04N 7/142* (2013.01); *G16H 40/67* (2018.01)

(58) Field of Classification Search
USPC ...................................................... 348/14.03
See application file for complete search history.

(56) References Cited

U.S. PATENT DOCUMENTS

| 6,128,317 A * | 10/2000 | Mackre | H04J 3/1688 370/466 |
| 2011/0267418 A1 * | 11/2011 | Galindo | G16H 40/67 348/14.04 |

OTHER PUBLICATIONS

Newton's Telecom Dictionary, 2006, Harry Newton, 22nd edition (Year: 2006).*

* cited by examiner

*Primary Examiner* — Amal S Zenati
(74) *Attorney, Agent, or Firm* — Wiley Rein LLP

(57) ABSTRACT

A telemedicine device is implemented in an integrated housing, which includes a display, input/output ports, a videoconferencing codec, and a codec-independent hardware user interface. A processor receives inputs through the user interface, translates them into instructions understandable by the codec, and sends the translated instruction to the codec for execution. The user interface can be standardized, such that it is identical regardless of the codec in use, and can group functions logically (e.g., call control, video functions, audio functions).

16 Claims, 5 Drawing Sheets

INTEGRATED TELEMEDICINE DEVICE

CROSS-REFERENCE TO RELATED APPLICATIONS

This application claims the benefit of U.S. provisional application No. 62/299,413, filed 24 Feb. 2016, which is hereby incorporated by reference as though fully set forth herein.

BACKGROUND

The instant disclosure relates to telemedicine. In particular, the instant disclosure relates to an integrated telemedicine device with a standardized, codec-independent hardware user interface.

The term "telemedicine" refers to the remote consultation and diagnosis of patients by means of telecommunications technology. Telemedicine encompasses everything from a simple telephone call between two parties (e.g., doctor and patient) to a more sophisticated real-time videoconference between two parties (e.g., a medical professional, such as a nurse or nurse practitioner, located with a patient at a first site, referred to herein as a "local" site, and a physician located elsewhere, referred to herein as a "remote" site).

These more sophisticated real-time videoconferences often employ codecs. "Codec" is an acronym for COder/DECoder, which is a device that encodes and decodes audio and video signals into a digital data stream for transmission across a network. A codec device can be used at either end of a network to enable a virtual live audio and video consultation between distant parties.

Extant codecs, however, vary significantly in their user interfaces between and across different makes and models. This variability can increase the complexity that a user encounters when moving from one codec to another and/or when encountering a new codec for the first time.

In addition, one common user interface for extant codecs is a software-driven, multi-level on-screen display. In such software-driven codec user interfaces, the selection of a desired function may require the user to drill down through multiple layers of menus in order to reach the appropriate control. Although this style of user interface is very common in visual communication equipment, because it allows the manufacturer to add features and functionality over time to the core product, it can lead to user confusion, for example when encountering an unfamiliar or new codec.

It would be desirable for a telemedicine device to have a standardized, hardware-based user interface that is not dependent upon the particular codec used therewith.

It would also be desirable for a telemedicine device to have a hardware-based user interface that utilizes a single push-button selection to access commonly-desired features.

It would also be desirable for a telemedicine device to limit the prominence of irrelevant and/or uncommonly-used functionality that might cause user confusion.

BRIEF SUMMARY

Disclosed herein is a telemedicine device implemented in an integrated housing. The telemedicine device includes: a display; a plurality of input/output ports; a videoconferencing codec; a codec-independent hardware user interface; and a processor. The processor is configured to receive an input through the codec-independent hardware user interface; to translate the received input into an instruction understandable by the videoconferencing codec; and to send the instruction to the videoconferencing codec.

According to aspects of the disclosure, the codec-independent hardware user interface includes: a codec-independent call control hardware user interface; a codec-independent video function hardware user interface; and a codec-independent audio function hardware user interface.

It is also contemplated that the processor can be configured to determine whether the received input is executable without inducing an error state; and to ignore the received input if the received input is not executable without inducing an error state.

In embodiments, the telemedicine device includes a camera and/or a microphone. The microphone can optionally be integrated into the camera.

An optional wireless remote control, including a codec-independent hardware user interface, is also contemplated. The codec-independent hardware user interface of the wireless remote control can mirror the codec-independent hardware user interface of the telemedicine device.

According to aspects of the disclosure, the processor is further configured to translate the received input into an instruction understandable by a peripheral device coupled to one of the plurality of input/output ports; and to send the instruction to the peripheral device.

Also disclosed herein is a telemedicine device including an integrated housing. The integrated housing, in turn, includes: a display; a plurality of input/output ports; a videoconferencing codec; a codec-independent hardware user interface; and a processor configured to translate user inputs received through the codec-independent hardware user interface into instructions understandable by the videoconferencing codec.

The codec-independent hardware user interface can include a plurality of codec-independent hardware control groupings, each codec-independent hardware control grouping including a plurality of hardware controls that have similar purposes. For example, the plurality of codec-independent hardware control groupings can include: a codec-independent hardware call control grouping; a codec-independent hardware video control grouping; and a codec-independent hardware audio control grouping.

A plurality of input/output devices, such as examination tools, cameras, microphones, and speakers, can be coupled to the plurality of input/output ports.

Optionally, the telemedicine device can include a wireless remote control, which also includes a codec-independent hardware user interface. The codec-independent hardware user interface of the wireless remote control can mirror the codec-independent hardware user interface of the telemedicine device.

The foregoing and other aspects, features, details, utilities, and advantages of the present invention will be apparent from reading the following description and claims, and from reviewing the accompanying drawings.

DETAILED DESCRIPTION

Figure 1:
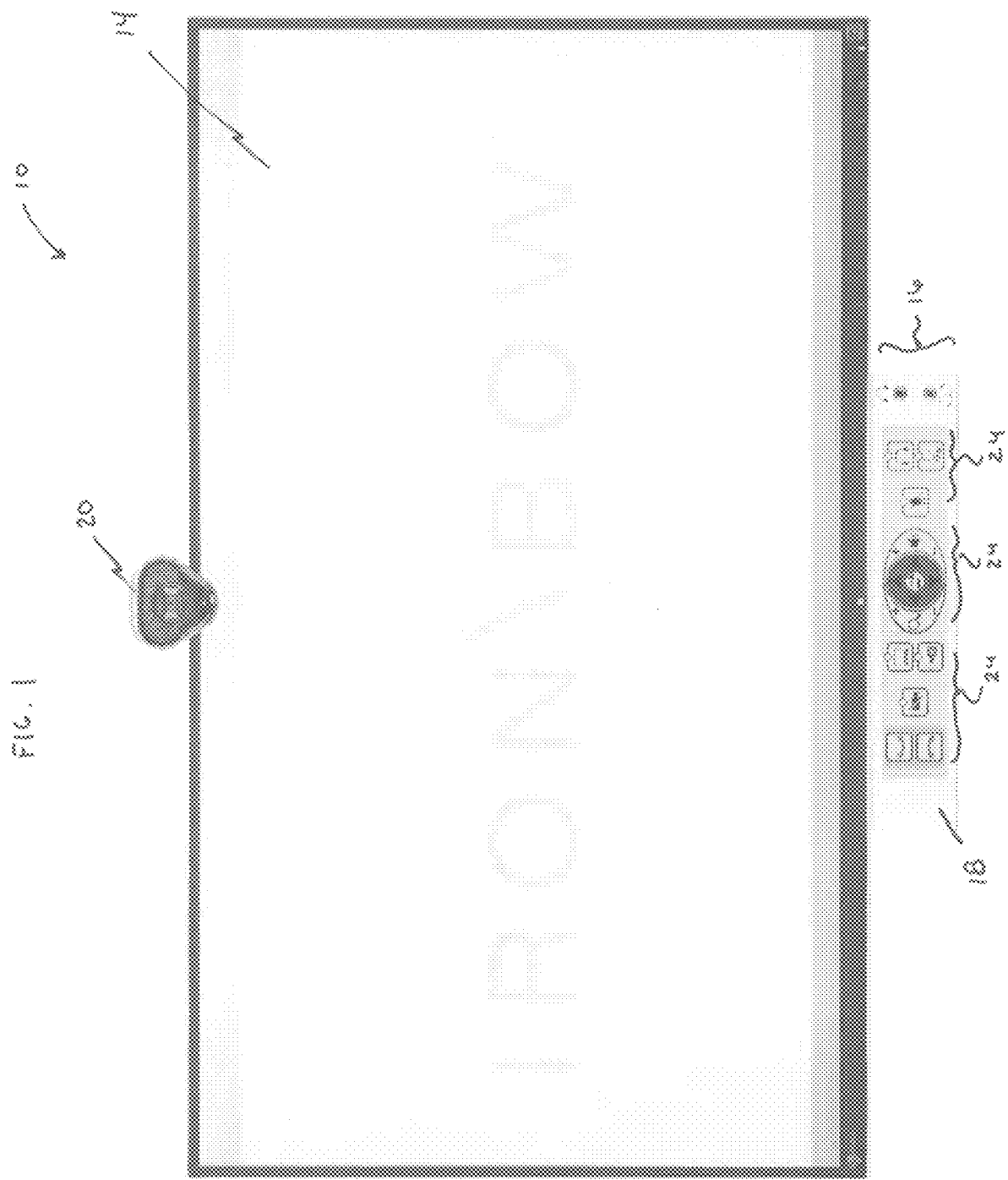
FIG. 1 is a front view of a telemedicine device according to embodiments of the instant disclosure.
Figure 2:
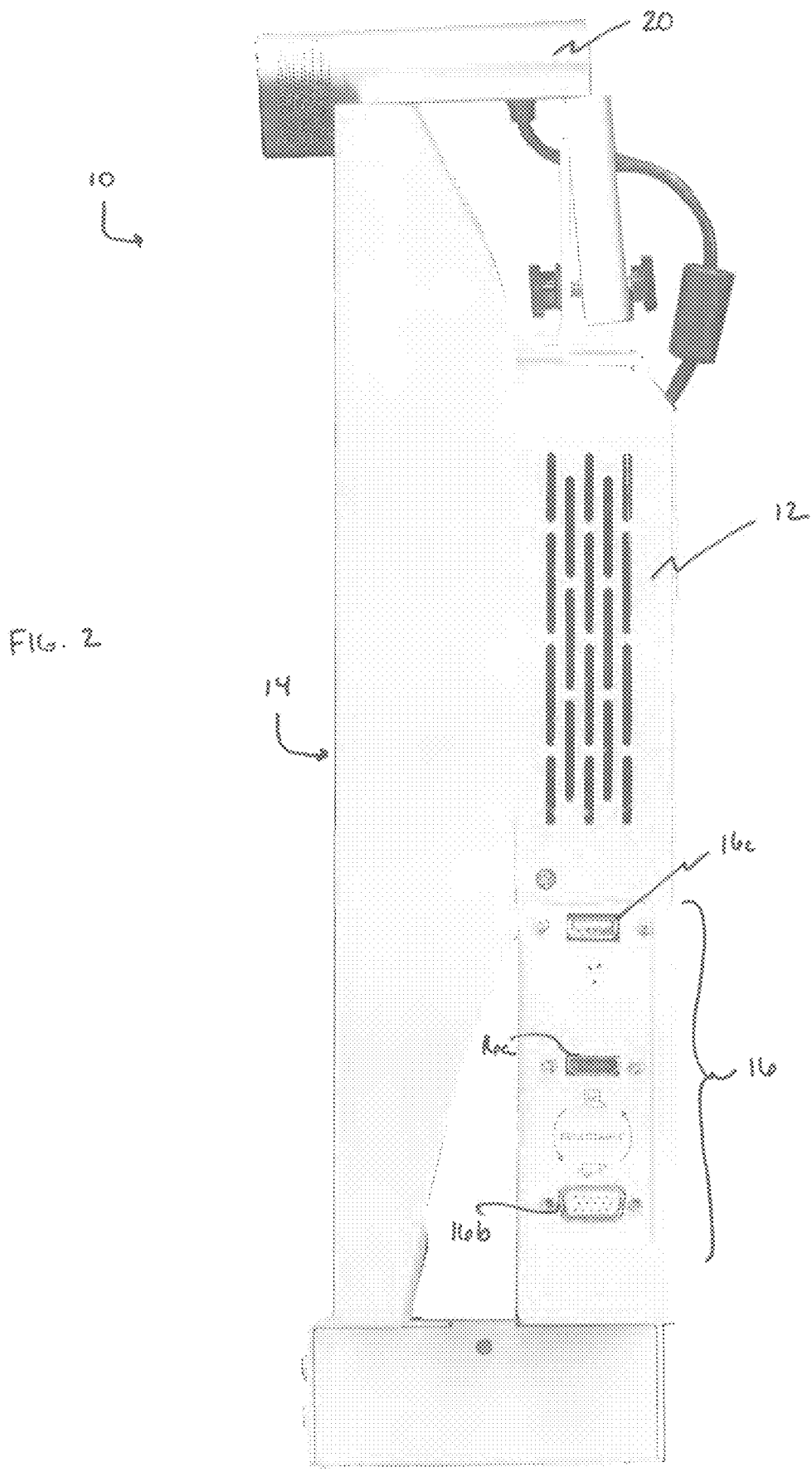
FIG. 2 is a left-side view of the telemedicine device of FIG. 1.
Figure 3:
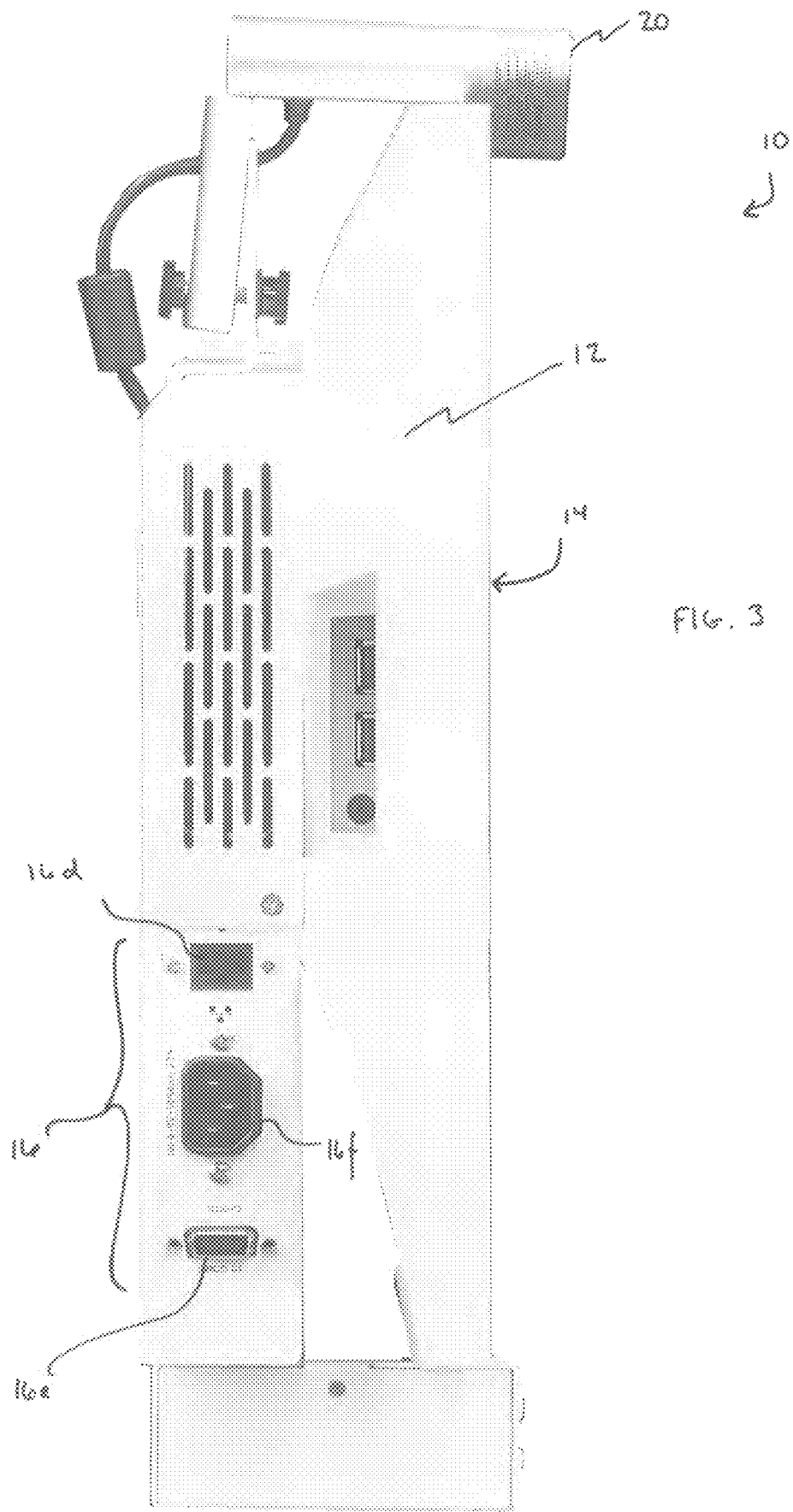
FIG. 3 is a right-side view of the telemedicine device of FIG. 1.

FIGS. 1-3 depict a telemedicine device 10, which is implemented in an integrated housing 12. Housing 12 of telemedicine device 10 incorporates a display 14, a plurality of input/output ("I/O") ports 16, and a user interface 18 implemented in hardware (as opposed, for example, to a software-based graphical user interface). A camera 20 (e.g., a static web camera or a web camera that includes additional functions, such as pan and/or tilt) is also shown.

Housing 12 can include hardware that enables telemedicine device 10 to be wall-mounted, cart-mounted, arm-mounted or the like. For example, the rear of housing 12 can include a plurality of VESA-compliant mounting holes. Alternatively, housing 12 can include a stand that supports telemedicine device 10 in an upright position. Cable management features are also contemplated.

As shown in FIG. 2, I/O ports 16 can include various analog and/or digital video inputs, such as an HDMI input 16a and/or a VGA input 16b. I/O ports 16 can also include an interface, such as a USB interface 16c, for the interconnection of peripherals (e.g., scopes and other examination devices), power adapters, and the like.

Additional I/O ports 16 are depicted in FIG. 3. For example, housing 12 can incorporate a network port 16d (e.g., for connection to a local area network) and an RS232 serial port 16e. Serial port 16e, for example, allows for bi-directional communication with an external device, such as an analog or digital matrix switch, which allows multiple peripherals (e.g., examination devices and/or scopes) to be connected to telemedicine device 10 through a single port. Serial port 16e can also be utilized, for example, to allow external or remote control (e.g., by a user at the remote site) of peripherals attached to telemedicine device 10.

It should be understood that an RS232 serial port is merely exemplary, and that other communication ports (e.g., IEEE 1394 ("FireWire"), universal serial bus ("USB"), or the like) and/or protocols (e.g., IEEE 802.11, Bluetooth, or the like) can be included in addition to or as an alternative to the depicted RS232 serial port. A power receptacle 16f is also included.

Figure 4:
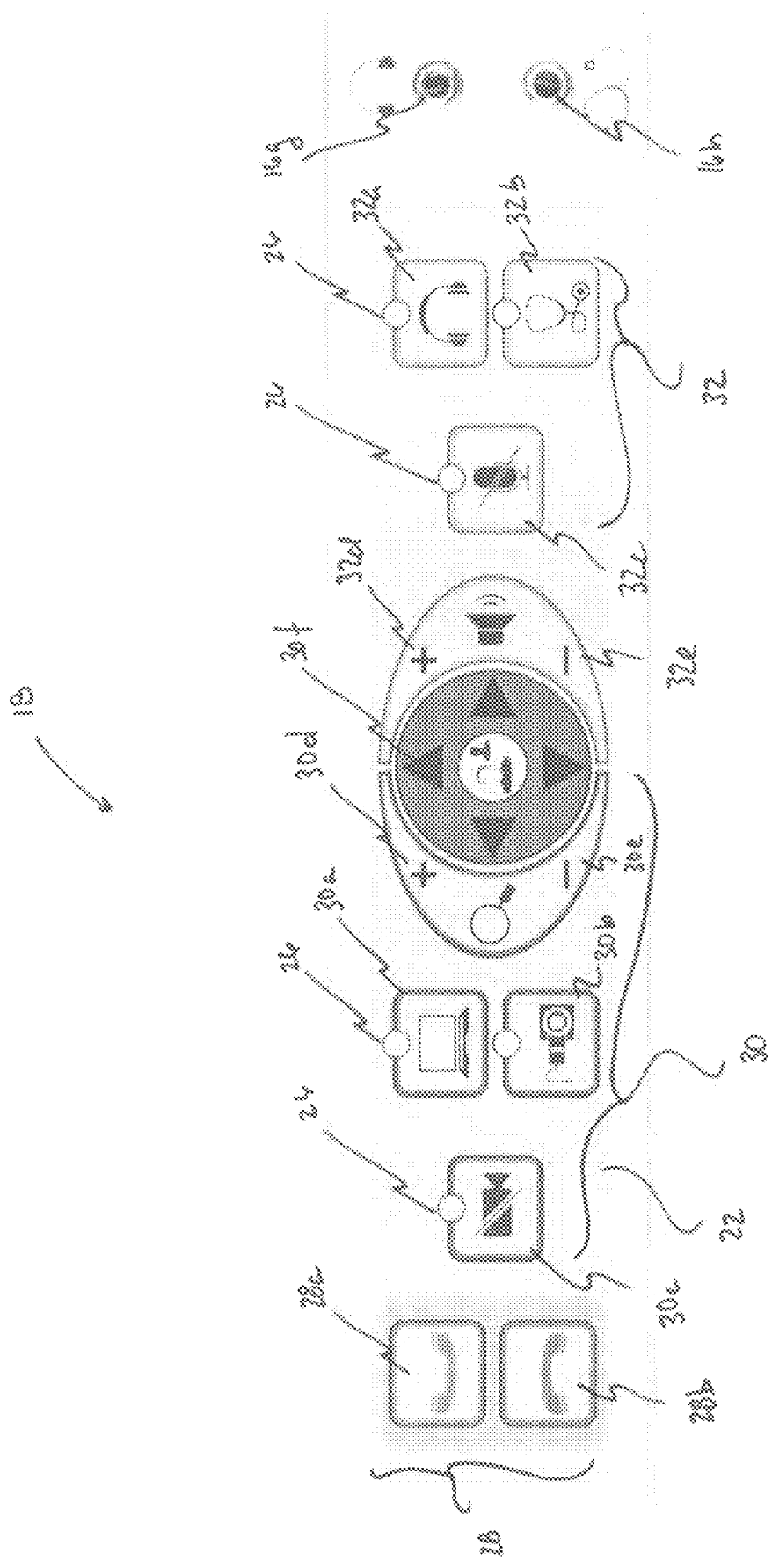
FIG. 4 is a close-up view of the hardware user interface of the telemedicine device of FIG. 1.

Further I/O ports are depicted in FIG. 4, which is a close-up view of the codec-independent hardware user interface 18. For example, a headphone port 16g and a stethoscope port 16h can be included. Likewise, codec-independent hardware user interface 18 can include one or more microphones and/or speakers to enable audio communications. In embodiments, it is contemplated that the microphones and/or speakers can be protected by one or more shields, for example to minimize the risk of fluid entering telemedicine device 10. Of course, the microphones and/or speakers can also be incorporated into camera 20.

According to aspects of the disclosure, interface 18 includes a tactile membrane 22, with a plurality of push-buttons 24 and associated indicators 26 (e.g., LEDs) to control various functions of telemedicine device 10, as discussed in greater detail below.

Advantageously, push-buttons 24 are grouped and presented in a logical and intuitive manner. For example, a call control hardware user interface 28 includes a "start call" button 28a (allowing the local user to initiate a call to or accept a call from a remote site) and an "end call" button 28b (allowing the local user to terminate the call with the remote site). Buttons 28a and 28b include graphics that will be familiar (e.g., an upward-facing green telephone handset for "start call" button 28a and a downward-facing red telephone handset for "end call" button 28b), which facilitates ease of use of telemedicine device 10.

A video function hardware user interface 30 includes a plurality of push-buttons to select, for example, between various video inputs to be broadcast to the remote site (e.g., a computer button 30a or a camera button 30b) or to "mute" the video entirely to the remote site (that is, to send a blank screen to the remote site) (e.g., button 30c). Video function hardware user interface 30 can also include zoom controls, such as a zoom in button 30d and a zoom out button 30e, to allow the local user to zoom in or out on aspects of the image. It is also contemplated to include navigation buttons 30f, which can be used, for example, to change the field of view of camera 20 (e.g., for a pan-and-tilt camera), again to allow the local user to focus on aspects of the image. In embodiments, all buttons that are part of video function hardware user interface 30 can be grouped together and/or marked with a common color scheme (e.g., they can all be outlined in blue).

Analogously, an audio function hardware user interface 32 can include a plurality of push-buttons to toggle, for example, between various audio inputs to be broadcast to the remote site (e.g., a headphone button 32a or a stethoscope button 32b) or to mute the audio input entirely to the remote site (e.g., button 32c). For example, according to aspects disclosed herein, selecting stethoscope button 32b can select an electronic stethoscope (connected, for example, through USB port 16c, stethoscope port 16h, or another suitable I/O port) as the audio source to be broadcast to the remote site, rather than using a microphone (which can be integrated into camera 20, integrated into telemedicine device 10, and/or externally coupled to telemedicine device 10, e.g., via USB port 16c).

According to other aspects disclosed herein, selecting headphone button 32a can feed audio from the remote site to a set of headphones, earbuds, or the like attached to headphone port 16g. This can facilitate a more private conversation between the local user and the remote site. It can also facilitate assistive listening.

Audio function hardware user interface 32 can also include a button to increase the volume 32d and a button to decrease the volume 32e. In embodiments, all buttons that are part of audio function hardware user interface 32 can be grouped together and/or marked with a common color scheme (e.g., they can all be outlined in orange).

Figure 5:
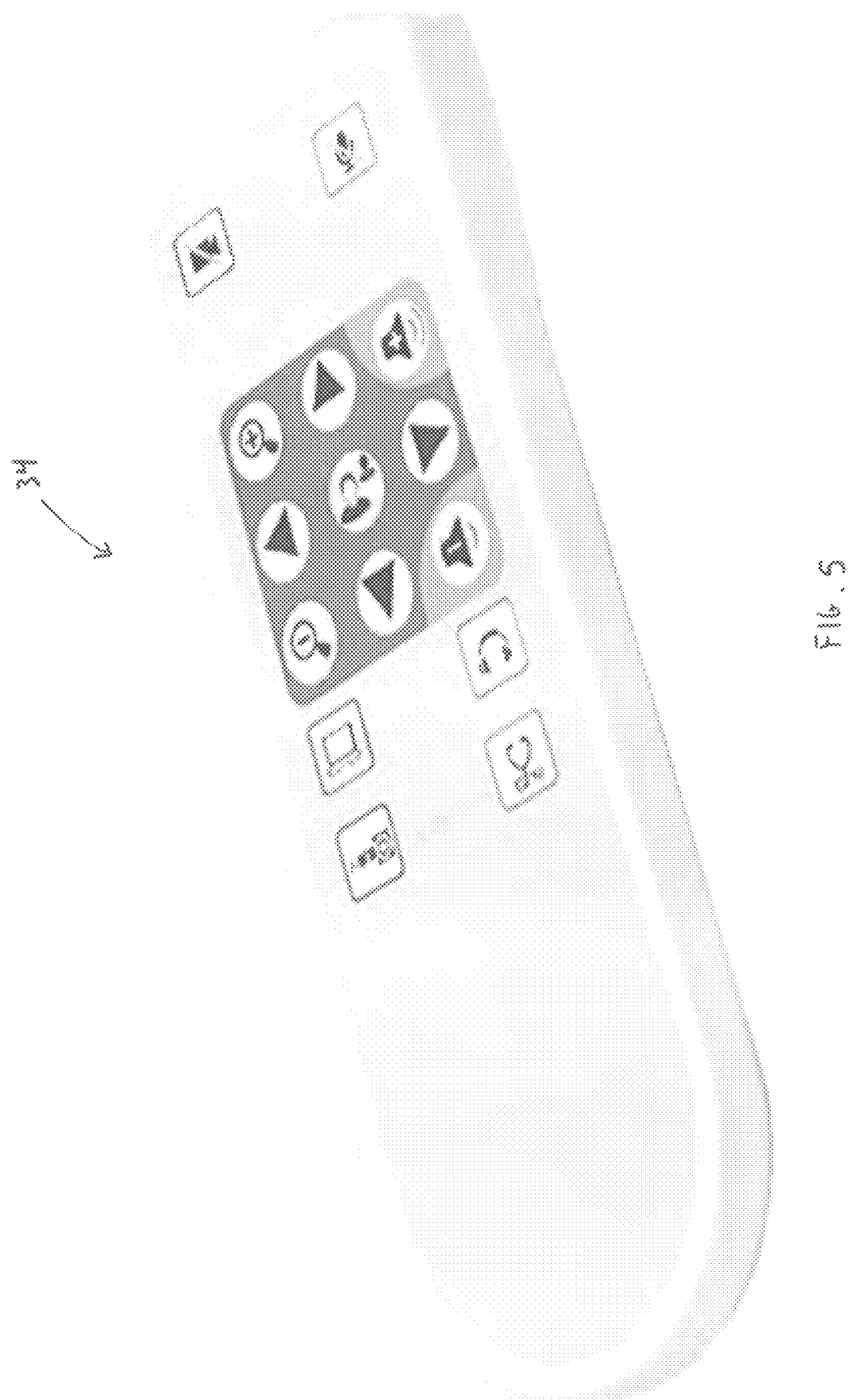
FIG. 5 depicts an exemplary wireless remote control according to aspects of the disclosure.

It is also contemplated that telemedicine device 10 can include a wireless remote control, such as the exemplary wireless remote control 34 depicted in FIG. 5. As shown in FIG. 5, the hardware user interface on wireless remote control 34 can generally mirror that of hardware user interface 18 integrated into housing 12 (e.g., similar and/or identical push-buttons can be provided on both hardware user interface 18 and remote control 34).

Wireless remote control 34 can communicate with telemedicine device 10 using any suitable communications protocol including, without limitation, infrared or radiofrequency protocols.

It should also be understood that wireless remote control 34 can include additional buttons to allow the local user to select between additional functions. For example, wireless remote control 34 can include a plurality of "speed dial" buttons that allow the local user to quickly connect to one or more remote sites.

As will be familiar to those of ordinary skill in the art, telemedicine device 10 utilizes a videoconferencing codec to broadcast audio and video to the remote site. In embodiments of the disclosure, the codec can be contained within housing 12, though it is also contemplated that the codec can be interfaced to housing device 12 as an external appliance. Suitable codecs include, without limitation, hardware codecs provided by Cisco, Polycom, LifeSize, Sony, and the like, as well as software codecs such as those provided by Vidyo, Zoom, VSEE, and the like, which would operate on a processor included within housing 12.

According to the instant teachings, hardware user interface 18 is codec-independent. As used herein, the term "codec-independent" means that the same layout of hardware user interface 18 can be used regardless of the particular codec utilized in conjunction therewith. As such, no additional user training would be required to utilize telemedicine device 10 as a result, for example, of upgrading or replacing the codec used therewith.

To achieve codec-independence, telemedicine device 10 can include a processor to receive and interpret inputs made at hardware user interface 18, to translate these inputs into instructions or commands understandable by the specific codec utilized with telemedicine device 10, and to send these instructions or commands to the codec for execution thereby. The term "processor," as used herein, includes central processing units (CPUs) either singly or in multiples (e.g., a parallel processing environment). It also includes both hardware- and software-based implementations.

It is also desirable for the processor to be configured to determine whether a particular input made at hardware user interface 18 can be executed without inducing an error state in telemedicine device 10, and to reject, ignore, or otherwise not execute such commands. For example, if the user selects computer input push-button 30a, with no computer attached (e.g., through HDMI input 16a), execution of the command would cause a blank screen and potentially lead to user confusion. Thus, the command should be rejected, ignored, or otherwise not executed.

Although several embodiments have been described above with a certain degree of particularity, those skilled in the art could make numerous alterations to the disclosed embodiments without departing from the spirit or scope of this invention.

For example, the "remote site" to which a "local user" connects through the use of "start call" button 28a need not be an individual user (e.g., a single remote physician). To the contrary, the "remote site" can include a network-based service, such as a conference bridge or recording server.

As another example, although certain groupings of controls are described herein (e.g., call control hardware user interface, video function hardware user interface, and audio function hardware user interface), these groupings are merely exemplary. It should be understood that other groupings are regarded as within the spirit and scope of the instant disclosure.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A telemedicine device implemented in an integrated housing, the telemedicine device comprising:
    a display;
    a plurality of input/output ports;
    a videoconferencing codec;
    a codec-independent hardware user interface; and
    a processor configured:
        to receive an input through the codec-independent hardware user interface; and
        to translate the received input into an instruction understandable by the videoconferencing codec; and
        to send the instruction to the videoconferencing codec.

2. The telemedicine device according to claim 1, wherein the codec-independent hardware user interface comprises:
    a codec-independent call control hardware user interface;
    a codec-independent video function hardware user interface; and
    a codec-independent audio function hardware user interface.

3. The telemedicine device according to claim 1, wherein the processor is further configured:
    to determine whether the received input is executable without inducing an error state; and
    to ignore the received input if the received input is not executable without inducing an error state.

4. The telemedicine device according to claim 1, further comprising a camera.

5. The telemedicine device according to claim 4, wherein the camera further comprises an integrated microphone.

6. The telemedicine device according to claim 1, further comprising a microphone.

7. The telemedicine device according to claim 1, further comprising a wireless remote control, the wireless remote control including a codec-independent hardware user interface.

8. The telemedicine device according to claim 5, wherein the codec-independent hardware user interface of the wireless remote control mirrors the codec-independent hardware user interface of the telemedicine device.

9. The telemedicine device according to claim 1, wherein the processor is further configured:
    to translate the received input into an instruction understandable by a peripheral device coupled to one of the plurality of input/output ports; and
    to send the instruction to the peripheral device.

10. A telemedicine device, comprising:
    an integrated housing, comprising:
        a display;
        a plurality of input/output ports;
        a videoconferencing codec;
        a codec-independent hardware user interface; and
        a processor configured to translate user inputs received through the codec-independent hardware user interface into instructions understandable by the videoconferencing codec.

11. The telemedicine device according to claim 10, wherein the codec-independent hardware user interface comprises a plurality of codec-independent hardware control groupings, and wherein each codec-independent hardware control grouping includes a plurality of hardware controls.

12. The telemedicine device according to claim 11, wherein the plurality of codec-independent hardware control groupings comprises:
- a codec-independent hardware call control grouping;
- a codec-independent hardware video control grouping; and
- a codec-independent hardware audio control grouping.

13. The telemedicine device according to claim 10, further comprising a plurality of input/output devices coupled to the plurality of input/output ports.

14. The telemedicine device according to claim 13, wherein the plurality of input/output devices are selected from the group consisting of examination tools, cameras, microphones, and speakers.

15. The telemedicine device according to claim 10, further comprising a wireless remote control including a codec-independent hardware user interface.

16. The telemedicine device according to claim 15, wherein the codec-independent hardware user interface of the wireless remote control mirrors the codec-independent hardware user interface of the telemedicine device.

\* \* \* \* \*